(12) United States Patent
Ahmed et al.

(10) Patent No.: US 9,155,830 B2
(45) Date of Patent: Oct. 13, 2015

(54) DEVICE FOR RADIATION-ACTIVATED LOCALIZED DELIVERY OF TREATMENT AGENTS

(71) Applicant: University of Miami, Miami, FL (US)

(72) Inventors: Mansoor M. Ahmed, Miami, FL (US); Xiaodong Wu, Miami, FL (US); Seema Gupta, Miami, FL (US); Alan Pollack, Miami, FL (US)

(73) Assignee: University of Miami, Miami, FL (US)

( * ) Notice: Subject to any disclaimer, the term of this patent is extended or adjusted under 35 U.S.C. 154(b) by 283 days.

(21) Appl. No.: 13/739,318

(22) Filed: Jan. 11, 2013

(65) Prior Publication Data

US 2013/0144212 A1     Jun. 6, 2013

Related U.S. Application Data

(63) Continuation-in-part of application No. PCT/US2011/040203, filed on Jun. 13, 2011.

(60) Provisional application No. 61/363,482, filed on Jul. 12, 2010.

(51) Int. Cl.
*A61M 5/142*     (2006.01)
*A61M 5/00*     (2006.01)
*A61K 47/48*     (2006.01)
*A61M 31/00*     (2006.01)

(52) U.S. Cl.
CPC ............ *A61M 5/00* (2013.01); *A61K 47/48861* (2013.01); *A61M 31/00* (2013.01); *A61M 5/14276* (2013.01)

(58) Field of Classification Search
CPC ..................... A61K 47/48861; A61M 5/14276
See application file for complete search history.

(56) References Cited

U.S. PATENT DOCUMENTS

| | | | |
|---|---|---|---|
| 2002/0055703 A1 | 5/2002 | Mori et al. | |
| 2004/0186417 A1 | 9/2004 | Phipps et al. | |
| 2007/0083186 A1* | 4/2007 | Carter et al. | 604/501 |
| 2008/0147186 A1* | 6/2008 | Joshi et al. | 623/11.11 |

* cited by examiner

*Primary Examiner* — Kevin C Sirmons
*Assistant Examiner* — Deanna K Hall
(74) *Attorney, Agent, or Firm* — Christopher & Weisberg, P.A.

(57) ABSTRACT

The present invention provides for a biocompatible drug delivery device for the targeted treatment of cancer that is implantable within the tumorous mass of a patient. In one embodiment, the device comprises two polarizable elements mechanically coupled by a connecting element. The device also comprises one or more cancer treatment agents. When the polarizable elements are depolarized, such as by the application of ionizing radiation, the two polarizable elements are repelled from each other and release the cancer treatment agent. In another embodiment, one or more treatment agents are expelled from a miniaturized syringe when internal pressure of the device is increased by the production of gas bubbles in response to the application of ionizing radiation.

20 Claims, 5 Drawing Sheets

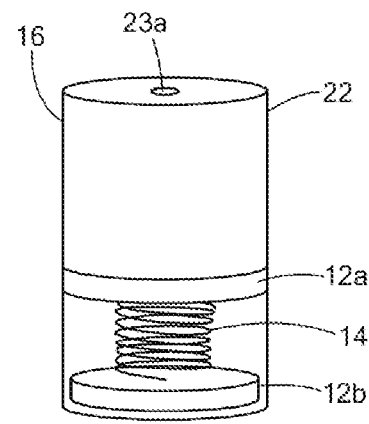
*FIG. 3A*
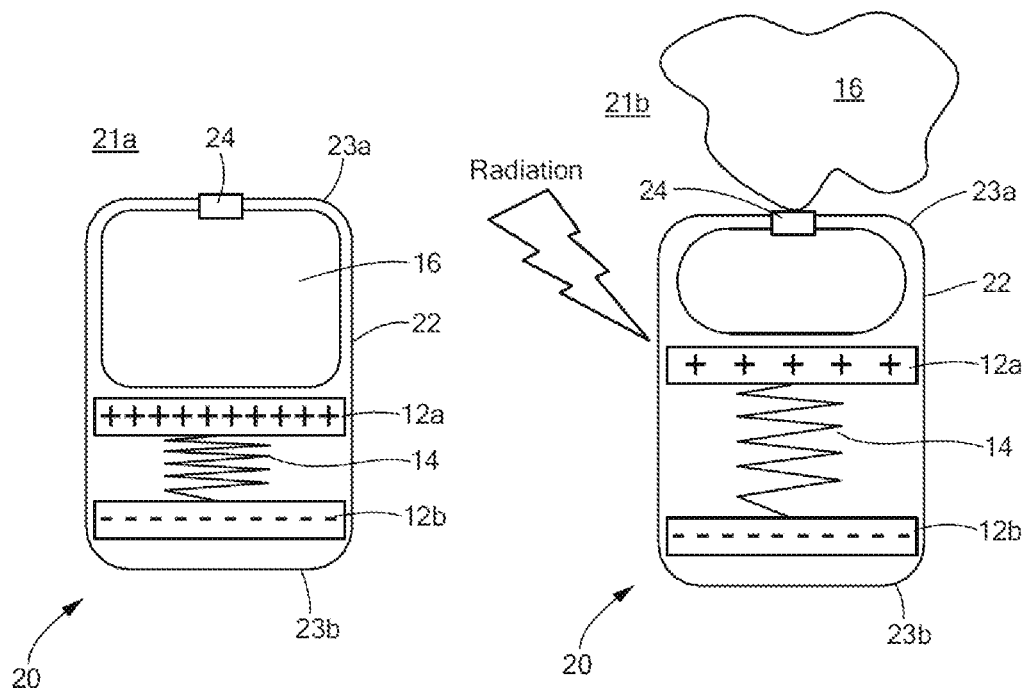
*FIG. 3B*     *FIG. 3C*

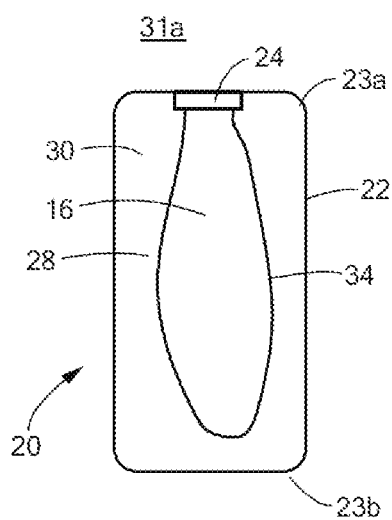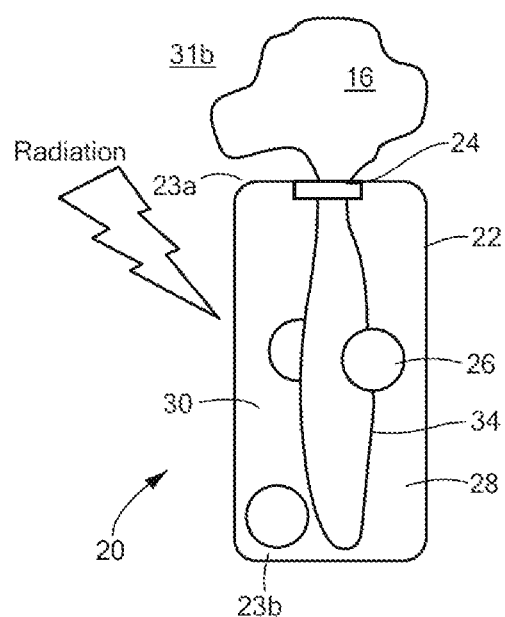
FIG. 6A
FIG. 6B

DEVICE FOR RADIATION-ACTIVATED LOCALIZED DELIVERY OF TREATMENT AGENTS

CROSS-REFERENCE TO RELATED APPLICATION

This application is a Continuation-in-Part-of and claims priority to International App. No. PCT/US2011/040203, filed Jun. 13, 2011, entitled DEVICE FOR RADIATION-ACTIVATED LOCALIZED DELIVERY OF TREATMENT AGENTS, which is related to and claims priority to U.S. Provisional App. No. 61/363,482, filed Jul. 12, 2010, entitled DEVICE FOR RADIATION-ACTIVATED LOCALIZED DELIVERY OF TREATMENT AGENTS, the entirety of all of which is incorporated herein by reference.

STATEMENT REGARDING FEDERALLY SPONSORED RESEARCH OR DEVELOPMENT n/a

FIELD OF THE INVENTION

The present invention relates to a method and system for storing and dispersing treatment agents.

BACKGROUND OF THE INVENTION

Cancer management is one particular area where local release of chemical agents for either therapeutic aim or for therapeutic sensitization has important advantages in targeted therapy. Traditionally, therapeutic cancer agents are administered in high concentration throughout the body in order to destroy cancer cells, translating to high toxicity and discomfort for the patient, mainly due to the effects on normal cells.

Two of the most common methods of treating cancer, chemotherapy and radiation therapy, are well known to have detrimental effects on the patient, such as anemia, extreme fatigue, hair loss, infection, memory changes, mouth and throat changes, nausea and vomiting, nerve changes, sexual and fertility changes, and swelling. These side effects arise from chemotherapy because the treatment kills rapidly dividing cells. Although these cells include most cancer cells, they also include cells that naturally divide rapidly, such as those in the digestive tract, hair follicles, and bone marrow. Although radiation therapy side effects are generally more localized, swelling, infertility, skin damage, and changes to the mouth and throat can occur, depending on the area treated. Other cancer treatment methods also are associated with important disadvantages. For example, traditional surgery involves long recovery time and can result in insufficient removal of all cancerous tissue; cryosurgery is limited to specific tumor types and long-term effectiveness has not been established; laser therapy involves extensive doctor training and expensive equipment, and the effects may not last long; and angiogenesis inhibitors may not kill tumors, but merely prevent new growth.

Miniaturized medical procedures are of great interest in cancer treatment, because they allow the precise treatment of cancerous cells with little or no effect on surrounding normal tissue. Furthermore, local release of chemical agents for either therapeutic aim or for therapeutic sensitization has important advantages in targeted cancer therapy. Micro-machined devices, such as micro-cantilevers, are currently used in a variety of different medical applications, such as for blood glucose monitoring, detection of chemical and biological warfare agents, and the detection of diseases and point mutations. Micro-cantilevers, which resemble planks, are commonly about 10-50 micrometers (μm) long and about 1 μm thick, and bend in response to different forces. A typical micro-cantilever may have a plurality of binding sites located on its surface to electively bind to target molecules, such as antibodies, proteins, or nucleic acid strands. The interactions between the binding sites and the target molecules change the mechanical response of the system such as its resonant vibration frequency.

Chemosensitizing drugs are used to make tumor cells more sensitive to chemotherapy, thereby allowing for smaller doses or fewer treatments of chemotherapy and a less severe effect on healthy tissue. Similarly, monoclonal antibodies delivered to cancer cells may also help target treatment. The application of monoclonal antibodies may function to make the cancer cells more visible to the patient's immune system, may block tumor growth factors, may prevent the growth of new blood vessels in the tumor, or may aid in the targeted delivery of radiation to cancer cells.

It would be advantageous to precisely deliver cancer treatment drugs to cancerous cells, and/or to deliver chemosensitizing agents and monoclonal antibodies (either alone or in combination) to aid in the targeting of other cancer treatments such as chemotherapy and radiation. Therefore, what is needed is a device that can store and deliver treatment agents to a target tissue site while minimizing damage to healthy tissue and adverse effects on the patient.

SUMMARY OF THE INVENTION

The present invention advantageously provides for a biocompatible drug delivery device for the targeted treatment of cancer. In one embodiment, the device may comprise two polarizable elements mechanically coupled by a connecting element. The first polarizable element and the second polarizable element may be composed of a dielectric material capable of carrying an electrical charge and may be depolarizable in response to an applied charge neutralization element. Alternatively, the polarizable elements may be semiconductors. A treatment agent may be disposed within the device, such that upon depolarization of the first and second polarizable elements, the treatment agent may be released when the electrostatic attraction between the first and second polarizable elements is overcome by the resistive force applied by the connecting element.

In another embodiment, the device may comprise an implantable miniaturized syringe that defines a one-way drug release valve and comprises two polarizable elements, mechanically coupled by a connecting element. The first polarizable element and the second polarizable element may be composed of a dielectric material capable of carrying electrical charges and may be depolarizable in response to an applied charge neutralization element. A treatment agent may be disposed within the device, such that upon depolarization of the first and second polarizable elements, the first and second polarizable elements repel each other and the treatment agent may be expelled from the one-way valve.

In another embodiment, the device may comprise an implantable miniaturized syringe that defines a one-way drug release valve and includes a medium in which tiny superheated liquid droplets are dispersed. A treatment agent may be disposed within the device. When exposed to ionizing radiation, the liquid droplets may vaporize and produce bubbles. The amount of bubbling may be directly proportional to the dose of ionizing radiation applied, and the bubbling may increase the internal pressure of the device. As the internal pressure increases, the treatment agent may be expelled from the device.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein

FIG. 3A is a further embodiment of a drug delivery device;

FIG. 3B is a cross-sectional view of the device of FIG. 3A in a first position;

FIG. 3C is a cross-sectional view of the device of FIG. 3A in a second position;

FIG. 6A is a cross-sectional view of a further embodiment of a drug delivery device, the device shown in a first position; and FIG. 6B is a cross-sectional view of the device of FIG. 6A in a second position.

DETAILED DESCRIPTION OF THE INVENTION

Figure 1:
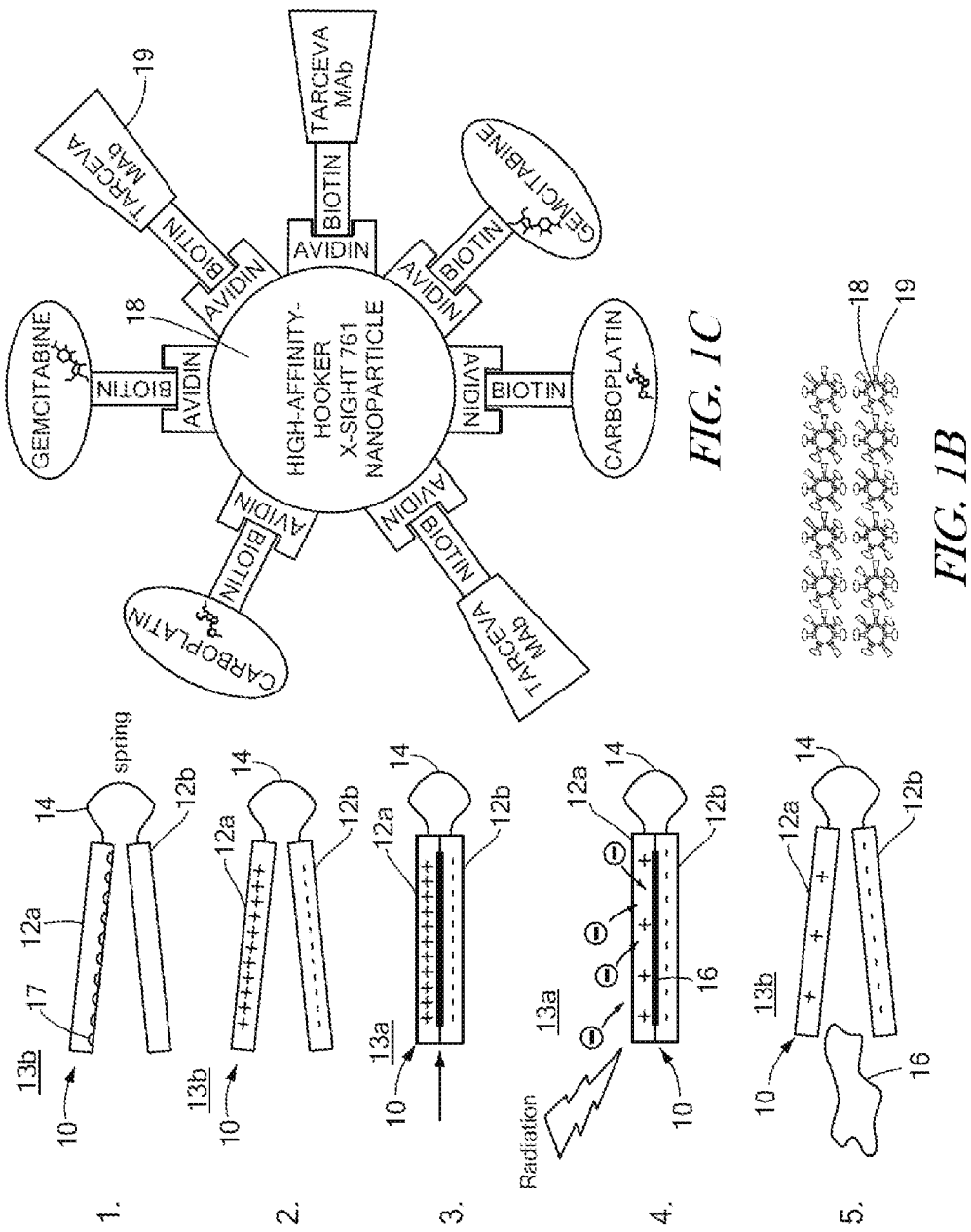
FIG. 1A is an embodiment of the drug delivery device and an exemplary treatment agent and targeting agent.
FIG. 1B is a stylized representation of nanoparticles of FIG. 1A.
FIG. 1C is a close-up, stylized representation of a nanoparticle of FIG. 1B.

Now referring to the drawings where like reference designators refer to like elements, FIGS. 1A-1C show an exemplary embodiment of a drug delivery device in accordance with the principles of the present invention and generally designated as "10." The device 10 may include a first polarizable element 12a and a second polarizable element 12b, each of which may be a dielectric material that has a quasi-permanent electric charge or dipole polarization (such as an electret), or any metallic element, such as a plate, capable of holding a charge. For example, as shown in FIG. 1A, the first polarizable element 12a may be positively charged and the second polarizable element 12b may be negatively charged. The first and second polarizable elements 12a, 12b may be oppositely charged, before insertion into a patient, causing them to engage each other by the electrostatic force.

Each polarizable element 12a, 12b defines a contact surface 13a, 13b, wherein the contact surface 13a of the first polarizable element 12a may be in contact with the contact surface 13b of the second polarizable element 12b. The first and second polarizable elements 12a, 12b may be any shape and may be sized on the milli-, micro-, or nano-scales. For example, in an exemplary embodiment the first and second polarizable elements 12a, 12b are substantially rectangular in shape and sized approximately 10-50 µm in length, approximately 1-5 µm in width, and approximately 1 µm thick to form a plate. The first and second polarizable elements 12a, 12b may further be comprised of a biocompatible and/or nonantigenic and/or biodegradable material to decrease the risk of a negative reaction from a patient to the material. For example, the first and second polarizable element 12a, 12b may be synthesized using Teflon AF or parylene HT. It is further contemplated that any number devices 10, including any number of the first and second polarizable elements 12a, 12b may be included.

Alternatively, the first and second polarizable elements 12a, 12b may be comprised of p-type and n-type semiconductors, such as silicon (Si). For example, the first polarizable element 12a may be composed of a p-type Si semiconductor and the second polarizable element 12b may be composed of an n-type Si semiconductor. P-type (positive) Si semiconductors are created by "doping" the silicon lattice with a small amount of impurity (dopant), usually boron or gallium, which each have three outer (valence) electrons (in contrast to silicon's four valence electrons. When there elements are added to the silicon lattice, the absence of a fourth electron in the dopant forms a hole in the lattice, creating an overall positive charge. N-type (negative) Si semiconductors are also created by doping the silicon lattice with a small amount of impurity, usually phosphorus or arsenic, which each have five valence electrons (in contrast to silicon's four valence electrons). When these elements are added to the silicon lattice, the "extra" electron is not bound so it moves through the lattice, creating an overall negative charge. The opposite charges between the p-type and the n-type Si polarizable elements causes them to engage each other by the electrostatic force, and the device remains closed. In the presence of ionizing radiation, however, the charge difference is reduced or neutralized, and the device 10 opens to release a treatment agent 16.

The first and second polarizable elements 12a, 12b may be movably coupled to each other by a connecting element 14, such as a spring mechanism, that separates the first and second polarizable elements 12a, 12b when the polarizable elements are depolarized. The connecting element 14, which may be composed non-metallic biocompatible materials, may be any mechanism that applies resistive forces in response to an applied force, and may be coupled to respective end portions of the first and second polarizable elements 12a, 12b. In an exemplary embodiment, the device 10 may define a first position 15a and a second position 15b. The first position 15a may include the first and second polarizable elements 12a, 12b being substantially parallel and in contact with each other in response to electrostatic forces generated when the first and second polarizable elements 12a, 12b are oppositely charged. The second position 15b may include the first and second polarizable elements 12a, 12b being repelled from each other when the first and second polarizable elements 12a, 12b at least partially carry the same charge (such as when a charge neutralization element is applied).

The treatment agent 16 may be contained within the device 10 when the device 10 is in the first position 15a, and the treatment agent 16 may be at least partially released from the device 10 when the device is in the second position 15b. For example, the connecting element 14 may be biased such that first and second polarizable elements 12a, 12b are urged away from each other. When the first and second polarizable elements 12a, 12b are charged, the electrostatic charges between the first and second polarizable elements 12a, 12b at least partially overcome the connecting element's 14 bias to engage the first and second polarizable elements 12a, 12b to each other, thereby closing the device (i.e. the device is in the first position 15a). When the charge of the first and second polarizable element 12a, 12b is at least partially neutralized, the bias of the connecting element 14 urges the first and second polarizable elements 12a, 12b away from each other, thereby opening the device (i.e. the device is in the second position 15b).

Continuing to refer to FIG. 1, the treatment agent 16 may be sandwiched between the contact surfaces 13a, 13b of the first and second polarizable elements 12a, 12b, when the device is in the first (closed) position, and released when the device is in the second (open) position. Alternatively, the treatment agent 16 may be deposited within one or more compartments or reservoirs 17 disposed on the contact surface 13a, 13b of at least one of the first and second polarizable elements 12a, 12b to store, for example, nano-sized particles in one or more closed nano- or micro-sized compartments (such as, for example, 0.02-1.0 µm). For example, uncharged devices 10 may be deposited within a pool of treatment agent 16. Upon the application of a charge, the first and second polarizable elements 12a, 12b close (i.e. the device is in the first position) and surround a portion of the treatment agent 16, either between the contact surfaces 13a, 13b of the first and second polarizable elements 12a, 12b or within the reservoirs 17 disposed within at least one contact surface 13a, 13b. The devices may then be extracted from the pool of treatment agent 16 for subsequent use.

The treatment agent 16 may be a therapeutic agent, such as a pharmaceutical or chemotherapy agent, or any other particle desired to be delivered to a target tissue site. The treatment agent may be a chemotherapy compound, therapy sensitizing agent, monoclonal antibody, any other compound suitable for the treatment of cancer, or any combination thereof. The treatment agent 16 may further be attached to antibodies, or other targeting agents, that target cancer cells that seek out and target cancer cells, and therefore facilitate in internalization of the drug resulting in higher treatment efficiency. The treatment agent 16 of FIG. 1A is shown in greater detail in FIGS. 1B and 1C. As shown in FIGS. 1B and 1C, the treatment agent 16 released from the device 10 may include a plurality of nanoparticles 18 bound to various treatment compounds 19. In an example for lung cancer treatment, erlotinib hydrochloride (Tarceva®) may be used as both the treatment agent 16 for destroying cancer cells, and as a target agent described above. In addition to Tarceva®, carboplatin (Paraplatin®) and gemcitabine (Gemzar®) may be bound to a nanoparticle, such as the X-Sight 761 High-Affinity Hooker Nanosphere, shown in FIG. 1C.

The device 10 having treatment agent 16 may be delivered to any part of the body through any number of delivery methods, including inhalation and injection. For example, for treatment of lung cancer, the device 10 may be inhaled and directly delivered to the lung tumors. While the device 10 may accumulate in both the tumor site and the normal tissue, it remains in the closed position unless a certain ionizing radiation dose is administered, thus preventing unnecessary exposure of treatment agent 16 to unintended tissue.

In an example for prostate cancer, devices 10 may have a carrying radio-sensitizer (not shown) and may further be attached to gold seeds (not shown) that are implanted in the prostate gland for image-guided radiation delivery. After attaching the devices 10 to the gold seeds, a thin layer of polymer is coated to the surface of the devices 10. The devices 10 can also be fabricated into small insolvent millimeter-sized polymer capsules that can be implanted into the prostate gland. Upon irradiation, the devices 10 within the capsules open and release the treatment agent 16. The polymer coating of the capsules may allow the treatment agent 16 to diffuse through while keeping the polarizable elements 12a, 12b and connecting elements 14 encapsulated.

Figure 2:
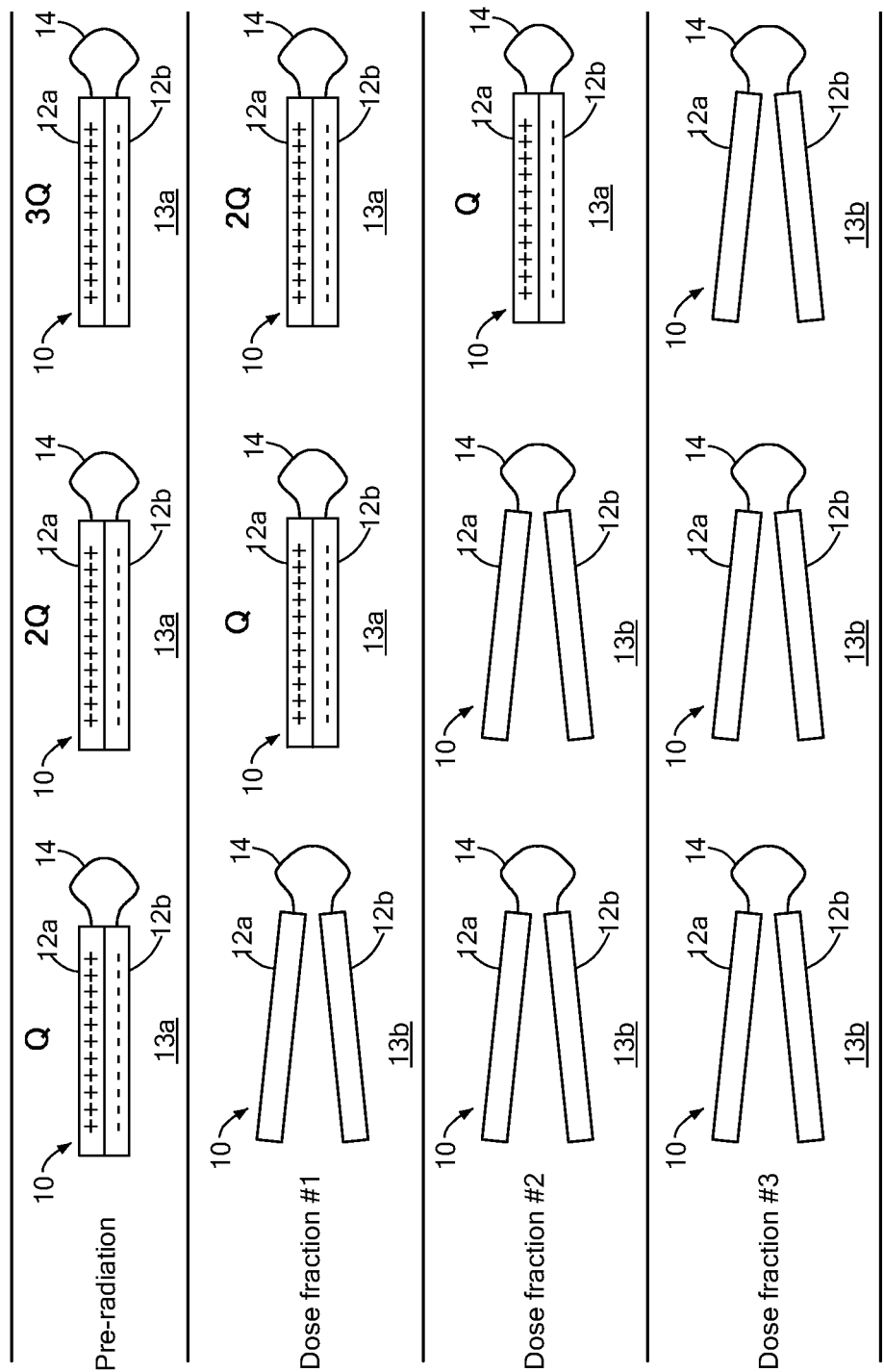
FIG. 2 is a chart showing the progressive activation of the drug delivery devices shown in FIG. 1.

Now referring to FIG. 2, each device 10 may be charged to a different level such that only a certain fraction of the devices 10 that may be deposited at a treatment site in a batch may be opened after each fraction of the ionizing radiation treatment. For example, assuming a ionizing radiation treatment of (n) fractions with fractional dose (d), the devices 10 may be calibrated to be charged with quantity (Q) for activating (opening) by dose (d). If (k) number of devices 10 are to be activated for each fraction of dose (d) delivery, (n) batches of devices 10 having (k) devices 10 per batch, with charges Q, 2Q, 3Q, ..., nQ, may be fabricated, mixed and, for example, made into a number of polymer capsules for implantation. After receiving the first dose fraction (d), (k) number of devices 10 that carry charge Q activates while the remainder of the devices 10 remains closed, but with each of their charges reduced by the amount Q. That is, the charge for all batches becomes 0Q, 1Q, 2Q, ..., (n−1)Q. After the second dose fraction (d), the batch that was pre-charged with 2Q now opens, and the remainder of the devices 10 remains closed with their charges further reduced by another quantity of Q. After the last fraction of dose (d) is delivered, the $n^{th}$ batch of the devices 10 opens.

Now referring to FIGS. 3A-3C, where a device 20 is shown according to the principles of the invention described above. The device 20 may be, for example, an ionizing-radiation-activated syringe, and may comprise a first and second polarizable element 12a, 12b (which may comprise electrets) and a connecting element 14. The device may define a first position 21a (as shown in FIG. 3B) and a second position 21b (as shown in FIG. 3C). The first position 21a may include the first and second polarizable elements 12a, 12b being in contact with each other in response to electrostatic forces generated when the first and second polarizable elements 12a, 12b are oppositely charged. The second position 21b (as shown in FIG. 3C) may include the first and second polarizable elements 12a, 12b being repelled from each other when the first and second polarizable elements 12a, 12b at least partially carry the same charge (such as when a charge neutralization element, such as ionizing radiation, is applied to the device 20).

A treatment agent 16 may be contained within the device 20 when the device 20 is in the first position 21a, and the treatment agent 16 may be at least partially expelled from the device 20 when the device 20 is in the second position 21b. For example, a charge neutralization element, such as ionizing radiation, may be applied to the device 20 by the method described above. The neutralization of the charges on the first and second polarizable elements 12a, 12b may cause the attraction forces between them to weaken, and the force applied by the connecting element 14 may overcome the attraction force between the first and second polarizable elements 12a, 12b. As the connecting element 14 pushes on the first polarizable element 12a, the treatment element may be expelled by mechanical force out of the device 20. In an exemplary embodiment, the volume of treatment agent 16 discharged by the device 20 may be proportional to the amount of charge neutralized by the ionizing radiation. As such, accurate dosing of the treatment element 16 may be achieved by applying a selected ionizing radiation dose.

Continuing to refer to FIG. 3, the first and second polarizable elements 12a, 12b may be substantially disc shaped and may have a diameter of approximately 1 mm. The first and second polarizable elements 12a, 12b are further disposed within a container 22, which may be substantially cylindrical in shape and define a first end 23a and second end 23b. The container 22 may further have a height of, for example, about 2 mm and a length of about 1 mm and be composed of biocompatible materials. The connecting element 14, such as a spring mechanism, may be vertically disposed between the first polarizable element 12a and the second polarizable element 12b such that a repellant force applied between polarizable elements 12a and 12b. A treatment agent 16 may also be disposed within the container 22, between the first polarizable element 12a and the first end 23a of the container 22.

The first end 23a of the container 22 may define a valve 24 in fluid communication with the treatment agent 16 so that the treatment agent 16 can be dispersed from the device 20 through the valve 24. For example, the valve 24 may be a one-way valve defined by the first end 23a of the container 22 such that when a sufficient force is applied from the first polarizable element 12a on the treatment agent 16, the treatment agent 16 may be expelled by mechanical force through the valve 24 and out of the container 22. If such a force is absent, the treatment agent 16 remains within the container 22.

Now referring to FIGS. 4A-6B, where a device 20 is shown according to the principles of the invention described above. The device 20 may be an ionizing-radiation-activated syringe. These embodiments, like the embodiments discussed above, may include a container 22 having a first end 23a defining a valve 24, a second end 23b, and may contain a treatment agent 16. The container 22 may further have a size of 1-2 mm in diameter and 4-8 mm in length, and may be composed of biocompatible materials. Unlike the embodiments discussed above, however, the device 20 does not include a first and second polarizable element 12a, 12b. Instead, the treatment agent 16 may be expelled by mechanical force through the valve 24 in response to an increase in internal pressure within the container 22, caused by bubbles 26 produced by the boiling of superheated liquid droplets dispersed within a bubble medium 28 in response to ionizing radiation. For example, when exposed to ionizing radiation, secondary charged particles produced in the bubble medium may interact with the superheated liquid droplets, causing them to vaporize and subsequently produce bubbles. The number of bubbles is correlated to the radiation dose.

When exposed to ionizing radiation, the superheated liquid droplets may be vaporized and produce bubbles 26. The superheated liquid droplets may be composed of liquid capable of generating bubbles when ionizing radiation moves through it, such as liquid hydrogen. The bubble medium may be any fluid or semifluid medium, such as an elastic polymer, capable of comprising the superheated liquid droplets and expanding as the superheated liquid droplets vaporize and produce bubbles. Alternatively, the bubble medium with superheated liquid droplets dispersed throughout may also comprise the treatment agent, the combination called herein the "bubble medium/treatment agent compound" and referred to as "29." The bubble medium/treatment agent compound 29 is expelled from the container 22 in response to ionizing radiation in substantially the same way that the treatment agent 16 is expelled from the container 22 when ionizing radiation is applied to the bubble medium 28.

When bubbles are generated in an enclosed container 22, the volume expansion may cause the internal pressure of the container 22 to increase, and this increased pressure may in turn expel the treatment agent out of the container 22 through the valve 24. Thus, the higher the dose of ionizing radiation, the more the internal pressure of the container 22 may be increased. The internal pressure of the container 22 may directly affect the amount of treatment agent 16 (or, alternatively, the bubble medium/treatment agent compound 29) expelled from the container 22 through the valve 24. The ionizing radiation dose may be administered in one application, or it may be administered in fractions of different or equal subdoses.

For the devices shown in FIGS. 4A-6B, the amount of treatment agent 16 (or, alternatively, the bubble medium/treatment agent compound 29) released may be directly proportional to the number of bubbles 26 generated, and may therefore be directly proportional to the ionizing radiation dose. The release of the treatment agent 16 (or, alternatively, the bubble medium/treatment agent compound 29) stops when pressure equilibrium is reached, and resumes when the next fraction of ionizing radiation dose is administered. For example, for a conventional ionizing radiation treatment with multiple fractions of small dose (1-2 Gy), the treatment agent 16 may be released at each fraction for up to 40 fractions. For hypofractionated ionizing radiation treatment, the treatment agent 16 may be released in 1 to 5 fractions in succession, activated by a fractional ionizing radiation dose of 5-20 Gy.

For the devices shown in FIGS. 4A-6C, the bubble medium may be a polymer, such as polymers with various concentrations of deuterium (for example, deuterium oxide ($D_2O$)), that also functions as a photon-to-neutron converter. Such a medium may allow the device to be sensitive to the photons of high-energy in the range of megaelectronvolts (MeV), and not just neutrons. For example, when high-energy (e.g., approximately 2.25 MeV and greater) X-rays strike the bubble medium, the deuterium may convert the photons to neutrons, and the resulting production of neutrons within the bubble medium may cause many of the superheated droplets to instantaneously change phase and become larger gas bubbles. The device's sensitivity to X-rays may be adjusted by varying the concentration of the deuterium in the polymer.

Figure 4A:
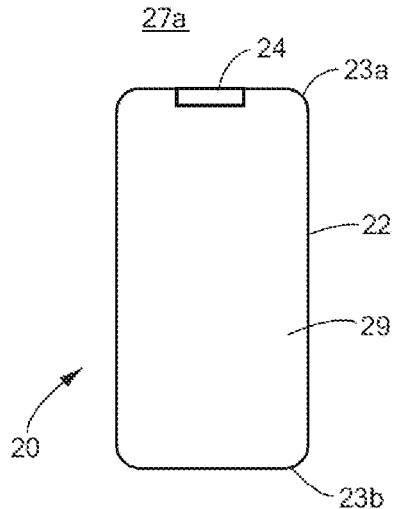
FIG. 4A is a cross-sectional view of a further embodiment of a drug delivery device, the device shown in a first position.
Figure 4B:
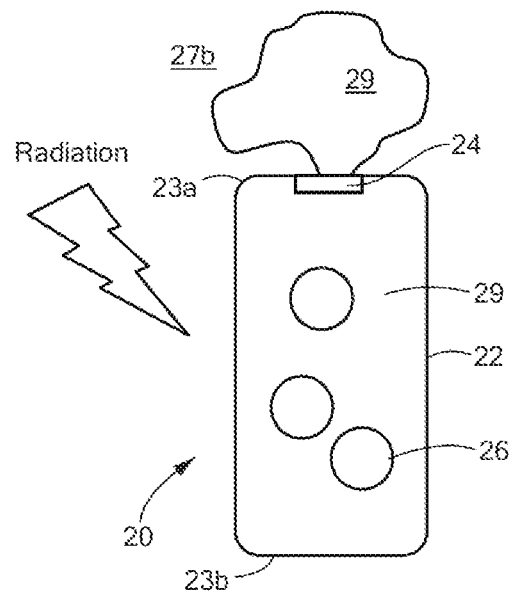
FIG. 4B is a cross-sectional view of the device of FIG. 4A in a second position.

Referring now specifically to FIGS. 4A and 4B, the container 22 may define a compartment 30 containing bubble medium/treatment agent compound 29. The device 20 may define a first position 27a (as shown in FIG. 4A) and a second position 27b (as shown in FIG. 4B). In the first position, the internal pressure within the container 22 is in a pressure equilibrium with the external pressure of an environment in which the container 22 is disposed, and the bubble medium/treatment agent compound 29 is contained within the device 20 (as shown in FIG. 4A). In the second position, the internal pressure within the container 22 is greater than the external pressure of the environment, and the bubble medium/treatment agent compound 29 is at least partially expelled from the device 20 through the valve 24 (as shown in FIG. 4B). The internal pressure within the container 22 is increased in response to ionizing radiation of the bubble medium/treatment agent compound 29 in substantially the same way as internal pressure is increased by the bubble medium 28, described above.

Figure 5A:
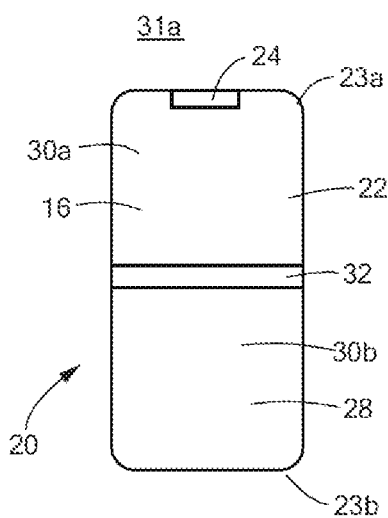
FIG. 5A is a cross-sectional view of a further embodiment of a drug delivery device, the device shown in a first position.

Referring now to FIGS. 5A-6B, the device 20 may define two compartments within the container 22. A first compartment 30a may contain an amount of treatment agent 16, while a second compartment 30b may contain an amount of bubble medium 28. The device 20 of FIGS. 5A-6B may define a first position 31a (as shown in FIGS. 5A and 6A) and a second position 31b (as shown in FIGS. 5B and 6B). In the first position 31a, the internal pressure within both the first compartment 30a and the second compartment 30b may be in a pressure equilibrium, and the treatment agent 16 may be contained within the device 20. In the second position 31b, the internal pressure of the second compartment 30b is greater than the internal pressure of the first compartment 30a, and the treatment agent 16 is at least partially expelled from the device 20 through the valve 24.

Figure 5B:
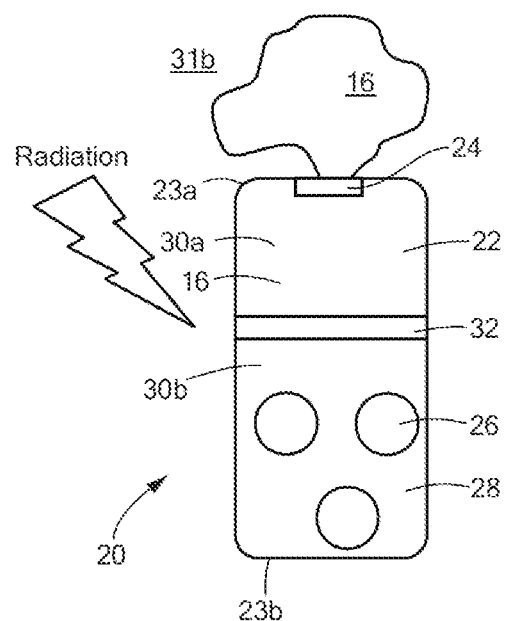
FIG. 5B is a cross-sectional view of the device of FIG. 5A in a second position.

Referring now to FIGS. 5A and 5B, a dividing material 32 may define the barrier between the first compartment 30a and the second compartment 30b. The dividing material 32 may be a solid plate with a shape that matches the internal diameter of the container 22, and which may freely move vertically within the container 22 in response to changes in the internal pressure difference between the first compartment 30a and the second compartment 30b. Alternatively, the dividing material 32 may be a flexible membrane that may be deformable into either the first compartment 30a or the second compartment 30b in response to changes in the internal pressure difference between the two compartments 30a and 30b. When internal pressure is increased in response to the application of ionizing radiation, the dividing material 32 may be moved or deformed into the first compartment 30a, and a dose of treatment agent 16 may be expelled out of the container 22 through the valve 24 (as shown in FIG. 5B). The amount of treatment agent 16 expelled may directly correlate to the ionizing radiation dose.

Referring now to FIGS. 6A and 6B, the first compartment 30a of the container 22 may comprise a deformable pouch 34 coupled to the valve 24. The deformable pouch 34 may be composed of any biocompatible material that is deformable in response to a change in internal pressure within the container 22. When internal pressure is increased in response to the application of ionizing radiation, the deformable pouch 34 may be compressed, thereby at least partially expelling the treatment agent 16 out of the container 22 through the valve 24. The amount of treatment agent 16 expelled may directly correlate to the ionizing radiation dose (as shown in FIG. 6B).

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A drug delivery device, comprising:
   a first polarizable element coupled to a second polarizable element, the first and second polarizable elements having different electric potentials and being depolarizable in response to an applied charge neutralization element, the first and second polarizable elements being sized to be disposed within human tissue; and
   a treatment agent disposed between the first and second polarizable elements,
   the device being transitionable between a first position and a second position, wherein:
      the first position includes the first and second polarizable elements being substantially parallel and in contact with each other in response to electrostatic forces generated when the first and second polarizable elements are oppositely charged; and
      the second position includes the first and second polarizable elements being repelled from each other when the first and second polarizable elements at least partially carry the same charge,
   the treatment agent being contained within the device when the device is in the first position, and the treatment agent being at least partially released from the device when the device is in the second position.

2. The device of claim 1, wherein the first and second polarizable elements are composed of Teflon AF or parylene HT.

3. The device of claim 1, wherein the first and second polarizable elements are composed of silicon, with the first polarizable element being composed of a p-type silicon and the second polarizable element being composed of an n-type silicon.

4. The device of claim 1, wherein the first and second polarizable element each define a contact surface in contact with the contact surface of the other polarizable element, the treatment agent being disposed between contact surfaces of the first and second polarizable elements.

5. The device of claim 1, wherein the first and second polarizable elements each define a contact surface in contact with the contact surface of the other polarizable element, at least one contact surface defining one or more reservoirs within which the treatment agent is disposed, the reservoirs being selected from the group comprising nano-sized reservoirs and micro-sized reservoirs.

6. The device of claim 1, wherein the treatment agent is a radiosensitizer and the device is attached to gold seeds.

7. The device of claim 1, wherein the treatment agent is a radiosensitizer and the device is included within small insolvent polymer capsules.

8. The device of claim 1, further comprising a connecting element, the first and second polarizable elements being coupled together by the connecting element.

9. The device of claim 8, wherein the connecting element is a spring.

10. The device of claim 8, wherein each of the first and second polarizable elements has a first end and a second end, the connecting element being coupled to the first end of each of the first and second polarizable elements.

11. The device of claim 10, wherein the connecting element has a bias to the second position, the electrostatic forces generated between the first and second polarizable elements when the device is in the first position being sufficient overcome the connecting bias of the connecting element.

12. The device of claim 1, wherein the treatment agent includes a plurality of nanoparticles, each of the plurality of nanoparticles being bound to at least one treatment compound.

13. The device of claim 12, wherein the at least one treatment compound is at least one of erlotinib hydrochloride, carboplatin, and gemcitabine.

14. The device of claim 1, wherein the charge neutralization element is ionizing radiation, the device being charged such that the device transitions from the first position to the second position when a desired dose of ionizing radiation is applied to the device.

15. A drug delivery device, comprising:
   a first polarizable element coupled to a second polarizable element, the first and second polarizable elements having different electric potentials and being depolarizable in response to an applied charge neutralization element, the first and second polarizable elements being sized to be disposed within human tissue; and
   a treatment agent disposed between the first and second polarizable elements, each of the first and second polarizable elements being a plate element.

16. The device of claim 15, wherein each of the first and second plate elements has a length of between approximately 10 μm and approximately 50 μm, a width of between approximately 1 μm and approximately 5 μm, and a thickness of approximately 1 μm.

17. A drug delivery device, comprising:
   a first polarizable plate element coupled to a second polarizable plate element, the first and second plate elements each having different electric potentials and being depolarizable in response to an applied charge neutralization element, the first and second plate elements being sized to be disposed within human tissue; and a treatment agent disposed between the first and second plate elements, the device being transitionable between a first position and a second position, the first and second plate elements in the first position being substantially parallel and in contact with each other in response to electrostatic forces generated when the first and second plate elements are oppositely charged; and the first and second plate elements in the second position being repelled from each other when the first and second plate elements at least partially carry the same charge, the treatment agent being contained within the device when the device is in the first position, and the treatment agent being at least partially released from the device when the device is in the second position.

18. The device of claim 17, wherein the treatment agent includes a plurality of nanoparticles, each of the plurality of nanoparticles being bound to at least one treatment compound.

19. The device of claim 18, wherein the at least one treatment compound is at least one of erlotinib hydrochloride, carboplatin, and gemcitabine.

20. A drug delivery device, comprising:

a first polarizable plate element, a second polarizable plate element, and a connecting element, the first plate element being coupled to the second plate element by the connecting element, the first and second plate elements each having different electric potentials and being depolarizable in response to an applied dose of ionizing radiation, the first and second plate elements being sized to be disposed within human tissue; and a treatment agent disposed between the first and second plate elements, the treatment agent including a plurality of nanoparticles each being bound to at least one treatment compound, the device being transitionable between a first position and a second position, the first and second plate elements in the first position being substantially parallel and in contact with each other in response to electrostatic forces generated when the first and second plate elements are oppositely charged; and the first and second plate elements in the second position being repelled from each other when the first and second plate elements at least partially carry the same charge, the treatment agent being contained within the device when the device is in the first position, and the treatment agent being at least partially released from the device when the device is in the second position.

* * * * *